United States Patent [19]

Goldin

[11] Patent Number: 4,891,185

[45] Date of Patent: Jan. 2, 1990

[54] HIGH RESOLUTION MONITORING DEVICE

[76] Inventor: Stanley M. Goldin, 10 Russell Rd., Lexington, Mass. 02173

[21] Appl. No.: 146,818

[22] Filed: Jan. 22, 1988

[51] Int. Cl.[4] .......................... B01L 3/00; G01N 1/10; G01N 23/00

[52] U.S. Cl. ........................................ 422/69; 422/99; 422/82; 422/101; 422/103; 436/50; 436/57; 436/178; 436/180; 210/658; 210/659; 73/863.23; 73/863.71; 137/628; 222/644

[58] Field of Search ...................... 422/67, 69, 72, 81, 422/82, 99, 101, 103; 436/44, 50, 57, 162, 178, 180, 527; 210/658, 659; 73/863.01, 863.23, 863.71, 863.73, 864.83; 137/624.12, 625.4, 628; 222/644

[56] References Cited

U.S. PATENT DOCUMENTS

| | | | |
|---|---|---|---|
| 2,551,281 | 5/1951 | Moses et al. ........................ | 422/91 |
| 2,741,544 | 4/1956 | Chaikin et al. ..................... | 422/91 |
| 3,567,392 | 3/1971 | Schulze .............................. | 436/122 |
| 3,667,917 | 6/1972 | Brandt .............................. | 210/658 X |
| 3,712,144 | 1/1973 | Kuzel et al. ....................... | 73/421 R |
| 3,754,867 | 8/1973 | Guenther ........................... | 422/91 |
| 3,825,410 | 7/1974 | Bagshawe .......................... | 436/57 |
| 3,912,452 | 10/1975 | Sodickson et al. ................ | 436/50 |
| 3,920,402 | 11/1975 | Afanasiev et al. ................ | 422/91 |
| 4,023,930 | 5/1977 | Blunck et al. ..................... | 436/44 |
| 4,052,162 | 10/1977 | Clarke ............................... | 422/81 |
| 4,073,621 | 2/1978 | Bull et al. ......................... | 422/87 |
| 4,115,067 | 9/1978 | Lyshkow ........................... | 422/56 |
| 4,180,383 | 12/1979 | Johnson ............................ | 422/101 X |
| 4,264,560 | 4/1981 | Natelson ........................... | 422/81 X |
| 4,292,409 | 9/1981 | Cremonesi ........................ | 435/288 |
| 4,459,360 | 7/1984 | Marinkovich ..................... | 436/513 |
| 4,552,723 | 11/1985 | Adams et al. ..................... | 422/66 |
| 4,558,013 | 12/1985 | Marinkovich et al. ........... | 436/513 |
| 4,603,114 | 7/1986 | Hood et al. ....................... | 422/101 X |
| 4,631,130 | 12/1986 | Watanabe .......................... | 210/343 X |
| 4,642,220 | 2/1987 | Björkman ......................... | 422/71 X |
| 4,643,878 | 2/1987 | Seiter et al. ...................... | 436/178 X |

FOREIGN PATENT DOCUMENTS 0164206 12/1985 European Pat. Off. ............ 422/116

OTHER PUBLICATIONS

Forbush, Anal. Biochem., "An Apparatus for Rapid Kinetic Analysis of Isotopic Efflux from Membrane Vesicles and of Ligand Dissociation from Membrane Proteins", 140:495–505 (1984).

Catalogue Excerpt advertising "Microporous Membrane Filtration".

Minnema et al., J. of Neuroscience Methods, "A Superfusion Apparatus for the Examination of Neurotransmitter Release from Synaptosomes", 14:193–206 (1985).

Redburn et al., J. of Neurochem., "Calcium-Dependent Release of Exogenously Loaded $\gamma$-Amino-[U-$^{14}$C]Butyrate from Synaptosomes: Time Course of Stimulation by Potassium, Veratridine, and the Calcium Ionophore, A23187", 26:297–303 (1976).

Redburn et al., Analytical Biochem., "Stimulus Secretion Coupling in Vitro: A Rapid Perfusion Apparatus for Monitoring Efflux of Transmitter Substances from Tissue Samples", 67:268–278 (1975).

Caviness et al., The J. of Pharmacology and Experimental Therapeutics, "Use of Rapid Superfusion to Differentiate the Release of Dopamine from Striatal Tissue Induced by Sympathomimetic Amines from Release Induced by Potassium", 223:90–96 (1982).

Primary Examiner—Michael S. Marcus
Assistant Examiner—Rebekah A. Griffith
Attorney, Agent, or Firm—Fish & Richardson

[57] ABSTRACT

A device for monitoring the release of a substance from a substrate, e.g., the release of ions through membranes, are disclosed.

18 Claims, 8 Drawing Sheets

HIGH RESOLUTION MONITORING DEVICE

This invention was made with support from the U.S. Government and the Government has certain rights in the invention.

BACKGROUND OF THE INVENTION

The invention relates to methods of monitoring the release of materials from supporting elements.

The contraction of skeletal muscle, the beating of the heart, and the secretion of hormones and neurotransmitters are controlled by the activity of ion channels. These channels are currently understood as being protein molecules embedded within the cellular membrane that allow the movement of ions across the membrane. The opening and closing of the channels, and the resulting release of ions and neurotransmitters, is known to occur on a subsecond timescale.

Forbush. 1984 Analytical Biochem. 140. 495, describes a device for monitoring the release of ions from membranes; the device obtained a time resolution of as low as approximately 10 msec.

SUMMARY OF THE INVENTION

In general, the invention features methods and devices for monitoring the release of a substance from a substrate, for example, the release of neurotransmitters and of ions such as $Na^+$ and $Ca^{+2}$ from structures surrounded by biological membranes. The substance is immobilized by the substrate when exposed to one set of conditions, and released from the substrate when exposed to a second set of conditions.

According to a first featured method, the substance immobilized by the substrate is supported, e.g., on a retainer in a sample chamber. The supported substance is then contacted with a flowing solution that carries away any substance released from the substrate. A stream of the solution flowing from the supported substance is contacted with a restricted zone of a substance absorbant. The substance absorbant absorbs some or all of the substance in the solution. By absorbs, it is meant that the substance absorbant retains the substance, e.g., by physical absorption or by chemical immobilization. The stream is continuously moved with respect to the substance absorbant to move the restricted zone across the substance absorbant to provide a substance absorbance pattern. The distribution of the substance in the absorbance pattern is then determined to provide a measure of the release of the substance from the substrate over a period of time.

In preferred embodiments of the first featured method, the substance absorbant is mounted on the surface of a rotating disc, and the absorbance pattern is a spiral track. Preferably the substance is radiolabeled, and the distribution of the radiolabel in the spiral track is determined, e.g., by generating an autoradiograph or by direct scintillation spectrophotometry, A time resolution as low as 2 msec can be achieved using the first featured method. Moreover, the absorbance pattern is generated quickly and efficiently on one convenient structure, the substance absorbant.

According to a second featured method, the substance immobilized by the substrate is supported on a depth filter, e.g., a glass fiber filter or a ceramic filter. The supported substance is then contacted with a flowing solution that carries away the substance released from the substrate, and a determination of whether the solution contains the substrate is made. The depth filter provides support for a substantial amount of substrate substance without clogging; for example, in one of the preferred methods 7 micrograms of protein can be supported per $mm^2$ of filter. Multiple filters can be stacked to support large quantities of the substance-substrate.

According to a third featured method, the substance immobilized by the substrate is supported on a retainer in a sample chamber. The sample chamber also has a solution entrance, a solution exit, and two solution flow paths connecting the entrance and exit. One path passes through the retainer, and the second path is relatively unobstructed and passes around the retainer, merging with the first flow path after the first flow path passes through the retainer. A solution is passed through the sample chamber and the flowing solution follows both flow paths, with solution following the first flow path contacting the supported substance to carry away the substance that has been released from the substrate. A determination of whether the solution exiting the sample chamber contains the substance is then made.

Because the second flow path is relatively unobstructed, solution flows through it faster than through the first flow path. The merger of the two solution flow paths has a flushing effect on the solution flowing in the first flow path, causing that solution to more rapidly exit the sample chamber. This substantially improves the time resolution of the release of the substance from the substrate, and may also improve the reproducibility of the quantification of the release.

In preferred embodiments of all the featured methods, the solution includes an agent being tested for its ability to cause the release of the substance from the substrate.

One featured device includes, in addition to a sample chamber and a solution collector, a solution source that includes (a) a plurality of valves corresponding to a plurality of solutions, the valves being responsive to control signals to deliver the solutions corresponding thereto to the solution collector, and (b) means for applying the control signals to the valves, the control signal applying means being programmable to selectively control the timing and duration of the delivery of solution by each valve.

In preferred embodiments of the device, the means for applying the control signal includes (a) means for generating a valve activating signal, (b) means for generating a signal to enable the valve activating signal to be coupled to the plurality of valves, and (c) means for switchably coupling the enabled valve activating signal to the plurality of valves to selectively cause the valves to deliver their respective solutions to the sample chamber, the coupling means being programmable to vary the timing and duration of the activation of each valve.

In some preferred embodiments in which the solution collector is a substance absorbant mounted on the surface of a rotating disc, the enable signal generating means is synchronized with the rotation of the rotating disc; and the means for switchably coupling the enabled valve activating signal to the plurality of valves is synchronized with the rotation of the rotating disc.

In other preferrred embodiments in which a spiral pattern is formed on the substance absorbant mounted on the rotating disc, the means that generates the valve enable signal is synchronized with the rotation of the rotating disc to produce the valve enable signal for a duration equal to the time required to generate the spiral pattern, and the means for switchably coupling the valve activating signal to the plurality of valves includes means for producing an output signal having a first state corresponding to the activation of a first one of the plurality of valves and a second state corresponding to the activation of a second one of the plurality of valves, the relative timing and durations of the first and second states being programmable; the valve activating signal is coupled to the first valve in response to the first state of the output signal, and the valve activating signal is coupled to the second valve in response to the second state of the output signal. In some of these preferred embodiments, the output signal producing means is also synchronized with the rotation of the rotating disc and is programmable to produce a pulse of the second state thereof at a predetermined time within the duration of the valve enable signal; the output signal producing means is alternately programmable to produce a pulse of the second state thereof during each revolution of the rotating disc, the pulses being synchronized with the rotation of rotating disc so that the pulses produced during a plurality of revolutions of the rotation disc are synchronized to be aligned on the spiral pattern; and the output signal producing means is alternately programmable to produce a series of pulses of the second state thereof during the formation of the spiral pattern.

The inventions provide convenient and rapid assays useful in determining the biological effects of new therapeutic agents on neurotransmitter release from nerve terminals, and on ion channels in intra- or extracellular membranes. Moreover, the information obtained should be useful in identifying normal and pathological responses mediated by such ion channels, and as a means of functionally determining rationales for the development of new drugs that modulate ion channel and/or nerve terminal responses.

Other features and advantages of the invention will be apparent from the description of the preferred embodiments thereof, and from the claims.

BRIEF DESCRIPTION OF THE DRAWINGS

In the drawings,

Referring to FIG. 1, a monitoring device 20 has a 12 inch diameter turntable 22 covered with an absorbant material 24. The turntable is connected to a programmable DC stepping motor (not shown) which when activated rotates the turntable. A sample chamber 26 has a 0.1-0.7 mm diameter solution outlet 27 arranged so that a solution exiting the sample chamber through the outlet contacts a restricted zone of the absorbant material. A DC motor 28 is connected to a worm gear 30 that moves the sample chamber in a plane parallel to that of the surface of the absorbant material opposite the sample chamber. A sensor (not shown) monitors the distance of the outlet 27 from the center of the turntable. The information is fed to the stepping motor of the turntable, which is programmed to increase the rotation rate of the turntable as the outlet 27 moves toward the center so that the radial velocity of absorbant material surface is constant with respect to the outlet 27. Other desirable configurations entail constant angular vs. linear velocity.

Figure 1:
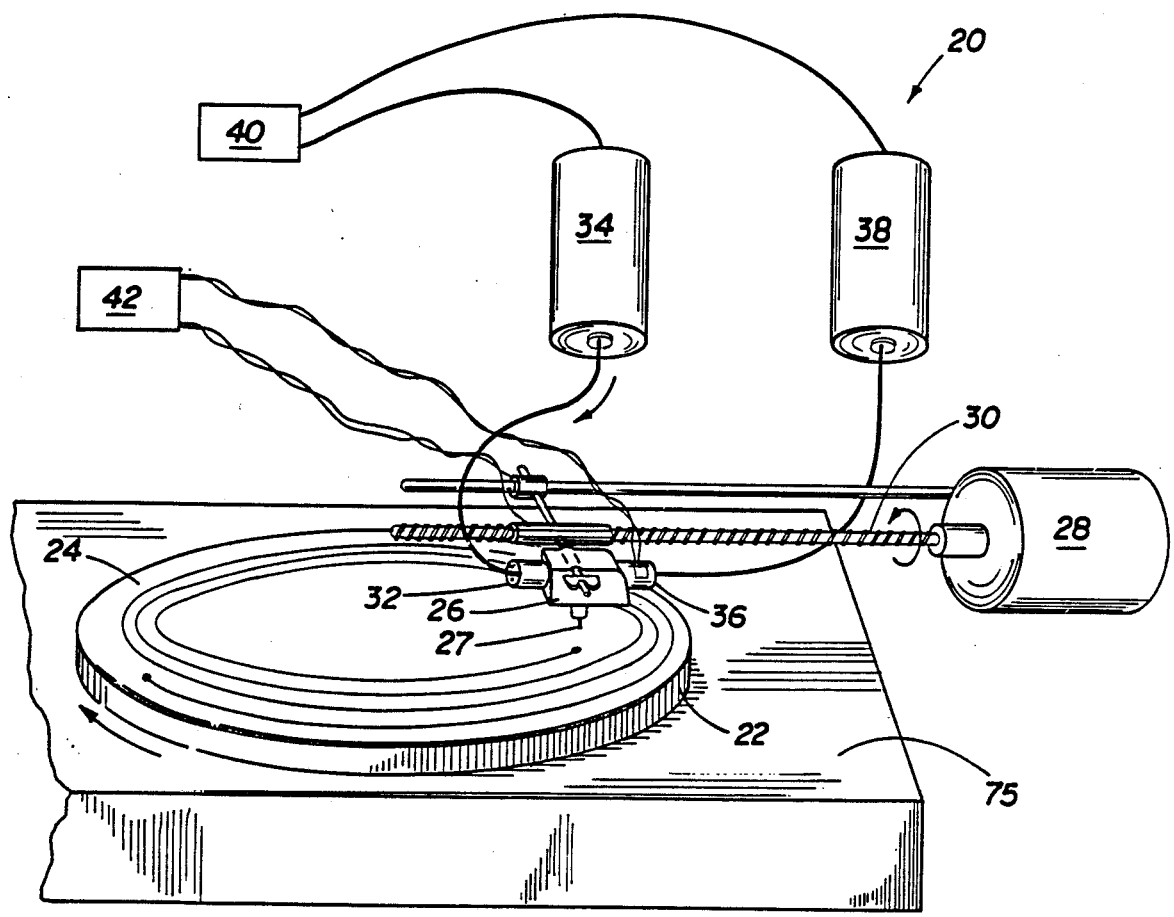
FIG. 1 is a perspective view of a preferred device.

The sample chamber has two solenoid valves 32, 36 through which each of two solutions can enter. (Other desirable configurations of this sample chamber, not shown, may have three or more solenoid valves through which three or more separate solutions can be introduced.) The inlet of valve 32 is connected via teflon tubing (3 mm O.D.×1.5 mm I.D.) to a 200 ml stainless steel reservoir 34 (available from Alloy Products Corp.) containing a first buffered solution. The inlet of valve 36 is connected via teflon tubing to a second stainless steel reservoir 38, which contains a second buffered solution that includes the agent to be tested. Both reservoirs are connected to a nitrogen pressure source 40. The solenoid valves are connected to valve control circuitry 42.

The absorbant material 24 absorbs some or all of the substance in the outlet solution. Preferred absorbant materials that absorb both the substance and the solution include sheets fabricated from polyacylamide, 1 mm thick Schiecher and Schuell thin layer chromatography paper, and Whatman #1 filter paper. An absorbant material that absorbs the substance but not the solution may also be used to give a higher concentration of the substance in a given volume of the absorbant. For example, where the substance is a charged species such as $Na^+$ or $Ca^{+2}$, the absorbant material can be a thin (0.1-0.2 mm), microporous ion exchange membrane filter (available from Schiecher and Schuell and from Millipore Corp.) that the substance binds to (chemical immobilization) while the solution passes through; a thicker material that absorbs the solvent can be placed underneath the ion exchange membrane.

Figure 2:
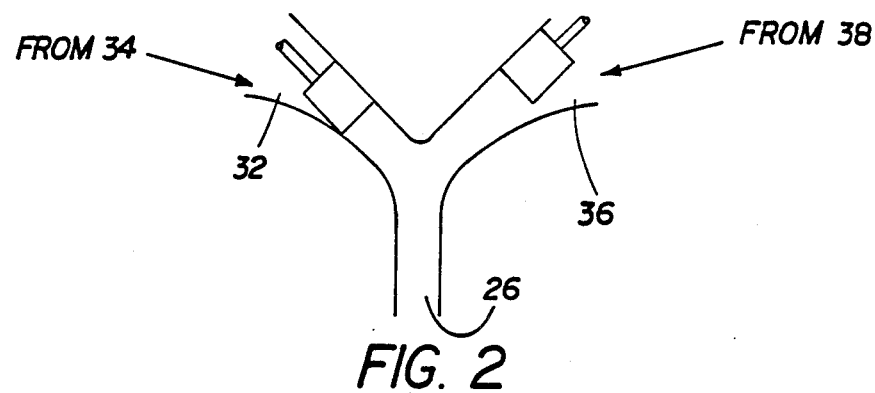
FIG. 2 is a sectional of the upper portion of the sample chamber.
Figure 3:
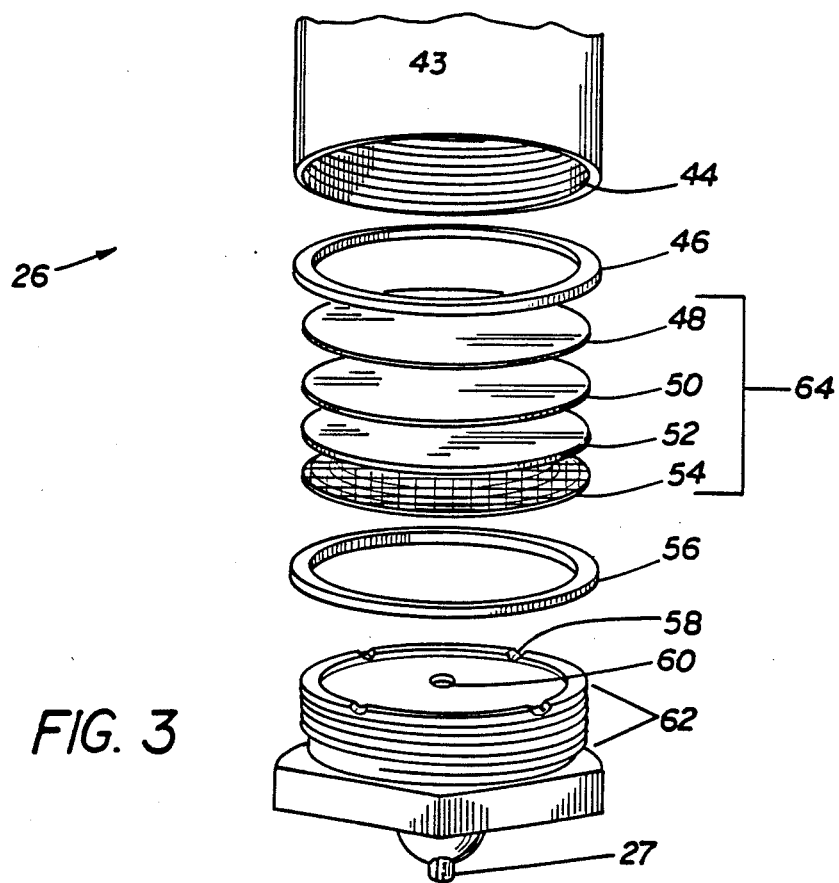
FIG. 3 is an exploded view of the bottom portion of the sample chamber.

Referring to FIGS. 2 and 3, the sample chamber includes a mixing chamber 43, between the two valves, having an internal mixing volume of approximately 2 ul; a threaded sample housing 44; 6 mm diameter stainless steel washers 46, 56; 6 mm diameter nitrocellulose membrane filters 48, 52 (e.g., Millipore Corp. SC filters cut to a 6 mm size); a 6 mm diameter depth filter 50 (more than one can be used to increase the sample capacity); a 6 mm support screen 54, cut from a fine stainless steel mesh; and a threaded outlet portion 62 (coated with Teflon tape for a watertight seal) having notches 58 for fluid channeling and a central solution exit 60. A two-valve mixing chamber assembly (which includes 26, 32, 36, and 43) is available from General Valve Corp., Fairfield, N.J. (part #9-352-900).

Depth filters are matrices of randomly-oriented fibers or beads pressed, wound, or otherwise bonded together into a tortuous maze of flow channels (definition obtained from Millipore Corp. Catalogue and Purchasing Guide, Lit. No. PA085, printed 9/85). A depth filter is capable of trapping the substrate in a three dimensional matrix thereby allowing a maximum amount of a substrate to be loaded onto the filter without causing a blockage (clogging) of the solution flow. The preferred depth filters are glass fiber filters such as Whatman GF/F filters; ceramic filters can also be used. Glass fiber filters are particularly desirable because of their flexibility, chemical inertness, and low cost.

The membrane filters 48, 52 above and below the depth filter protect the substrate from damage from the high fluid shear rates generated in the sample chamber, and further prevent damage or dimensional changes in the depth filter due to fluid shear.

When the sample chamber is assembled, the amount of dead volume above and below the depth filter 50 is low, i.e., less than 50 mm$^3$. A low dead volume is desirable to minimize the time required for changes between the solution streams and for exit of the released substance from the chamber. The diameter of the depth filter that is exposed to the flowing solution is approximately 3 mm, as the washers 46, 56 press against the filter assembly 64 to reduce the exposed diameter.

Solution flowing from the mixing chamber 43 will follow two flow paths. One flow path passes through the filter assembly 64 and exits at outlet 60. The second flow path circumvents the filter assembly by exiting the mixing chamber through notches or channels (not shown) in the inner surface of threaded valve assembly 44; the solution following this path, after flowing around the filter assembly, passes through notches 58 to mix with the solution that follows the flow path through the filter assembly. The second flow path is relatively unobstructed, i.e., it does not pass through a depth filter loaded with a substrate, and therefore the solution flow rate is faster than in the first flow path. The joining of the faster-flowing solution with the solution following the first path creates a flushing effect on the latter, causing solution following the first, more obstructed path to exit the sample chamber at a faster rate.

Figure 4:
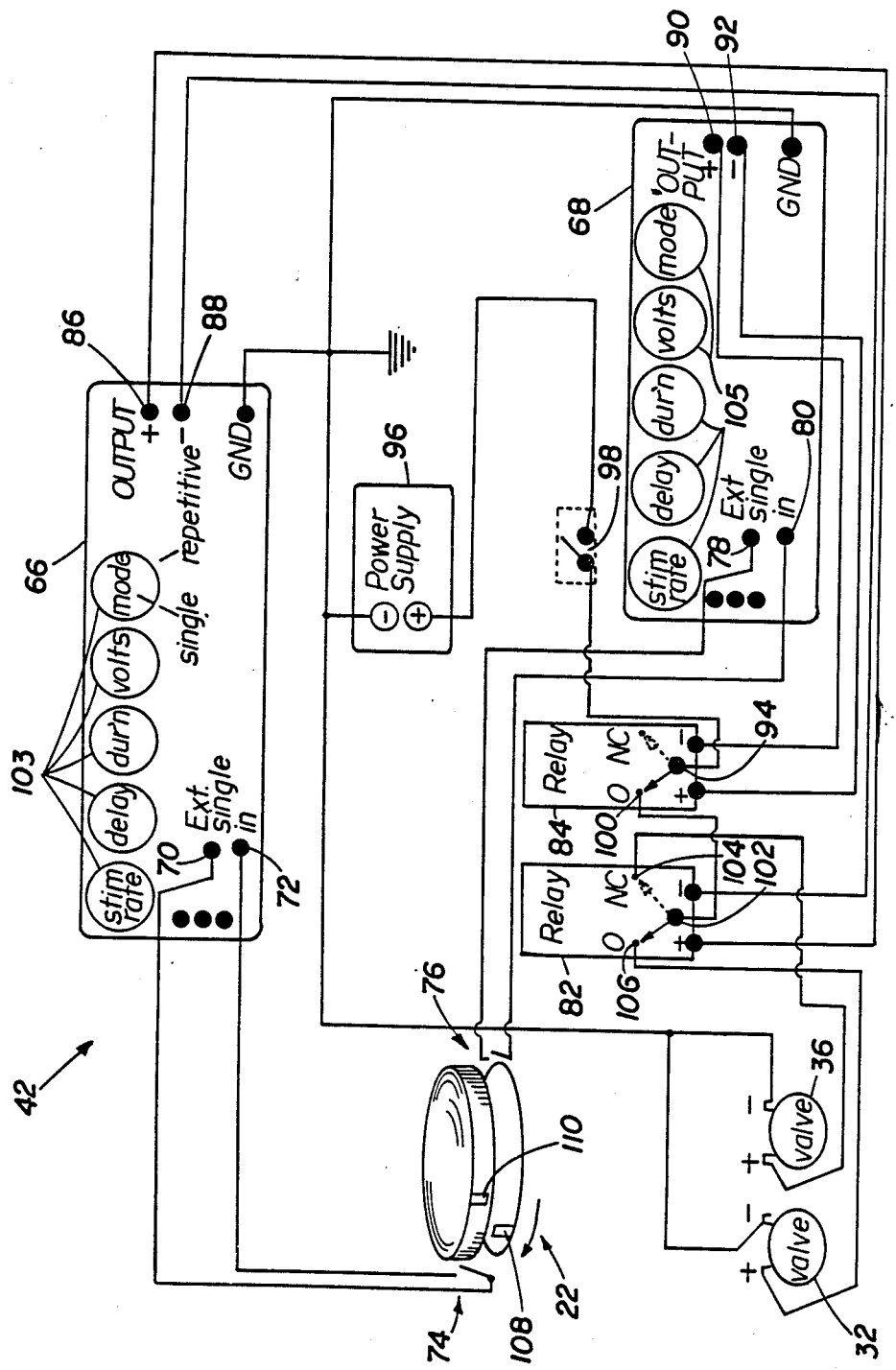
FIG. 4 is the valve control circuitry for the FIG. 1 device.
Figure 5:
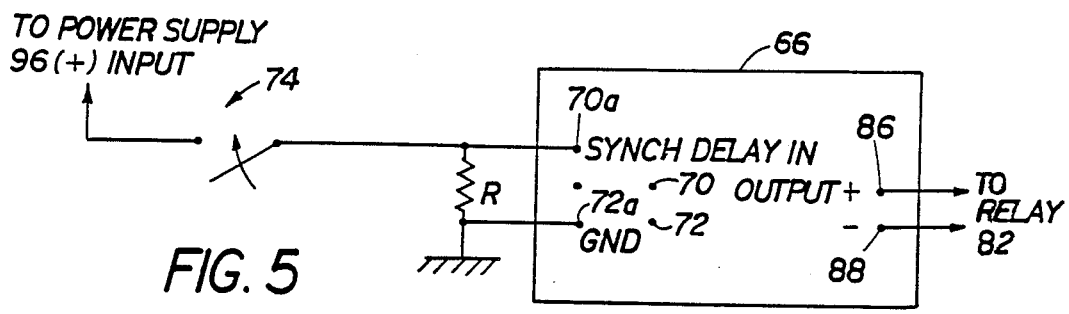
FIG. 5 is a modification to the valve control circuitry of FIG. 4.
Figure 7:
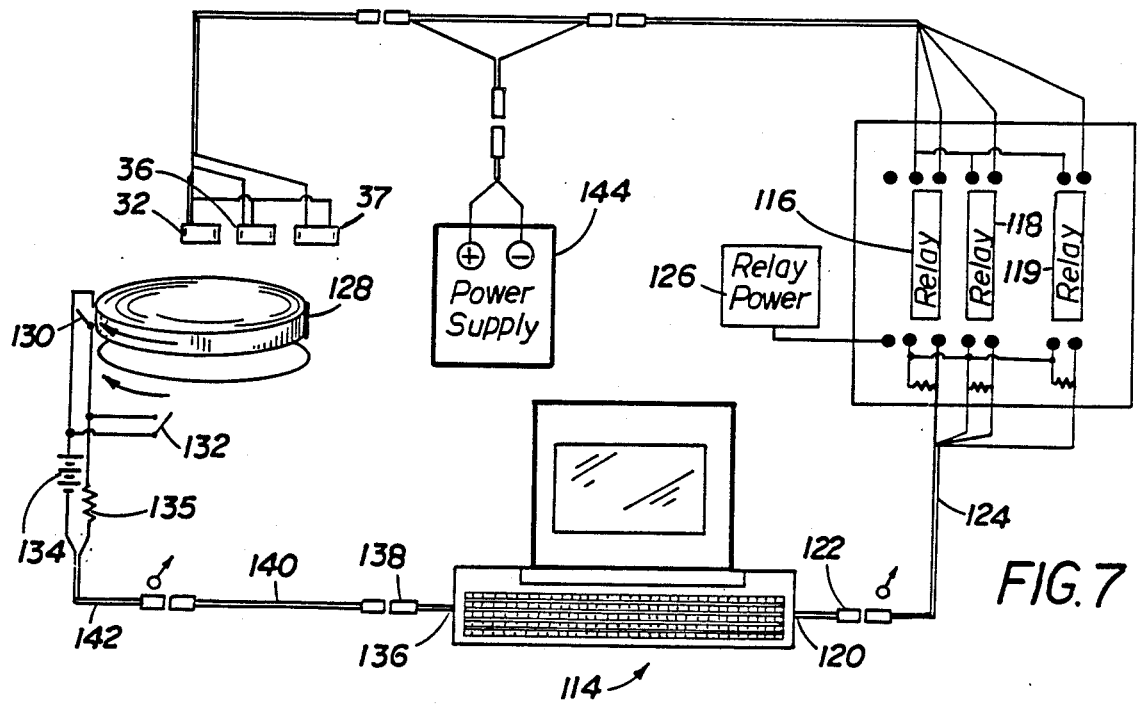
FIG. 7 is an alternate valve control circuitry.

Referring to FIG. 4, valve control circuitry 42 comprises a pair of commercially available stimulators 66, 68, here model S44 stimulators manufactured by Grass Medical Instruments, Inc., of Quincy, Mass., for controlling the operation of stimulating agent valve 32 and buffer valve 36 via relays 82, 84. Briefly, stimulator 68 controls relay 84 to couple and decouple valve operating power (from power supply 96 and manual switch 98) to and from relay 82, which responds to the output of stimulator 66 to apply the operating power to open either stimulating agent valve 32 or buffer valve 36.

Stimulator 66 includes a pair of input ports 70, 72, labeled "Ext. Single In", connected to the terminals of a magnetic switch 74 disposed on the base 75 (FIG.. 1) of turntable 22. The Ext. Single In ports 78, 80 of stimulator 68 are connected to the terminals of magnetic switch 76 on turntable base 75. Switches 74, 76 are actuated by a pair of permanent magnets 110, 108, respectively, on turntable 22 as the turntable rotates, as discussed in detail below.

The (+) and (−) output ports 86, 88 of stimulator 66 are connected to the (+) and (−) control terminals of relay 82. Likewise, the (+) and (−) control terminals of relay 84 are driven by the (+) and (−) output terminals 90, 92 of stimulator 68. Relays 82, 84 may be any suitable switching devices, for example, mercury wetted contact relays (switching speed, approximately 1 msec.) manufactured by Newark Electronics of Newark, N.J., as model GI Clare No. HGJM 51111 X00. The common terminal 94 of relay 84 is connected to the positive output of 12 volt DC power supply 96 through manual switch 98. The normally open terminal 100 (i.e., the terminal which is decoupled from common terminal 94 in the absence of a stimulating signal to the (+) and (−) inputs of relay 84) is connected to common terminal 102 of relay 82, the normally closed (NC) terminal 104 of which is connected to the (+) input terminal of buffer value 36. The (+) input terminal of stimulating agent valve 32 receives its input from the normally open terminal 106 of relay 82. The (−) inputs of values 32, 36 are connected to a reference potential (e.g. ground) along with the (−) terminal of power supply 96 and the GND terminals of stimulators 66, 68.

In operation, stimulators 66, 68 produce output signals having characteristics in accordance with the setting of programming controls 103, 105, respectively, to enable a number of stimulus and buffer protocols to be executed. Specifically, programming controls 103, 105 allow the operator to vary, for each stimulator, the amplitude ("volts") of the output signal, the delay between an imput stimulus (e.g., the closing of switches 74, 76) and the start of the output signal, and the duration ("dur'n") of the output signal. Additionally, as discussed in detail below, each stimulator 66, 68 may be set to produce either a single output pulse (i.e. a DC signal for the programmed duration) or a series of repetitive pulses, via "mode" controls 103, 105, respectively. As discussed below, however, typically stimulator 66 is the only device which is used in the repetitive mode. In the repetitive mode, the pulse width and frequency of the output pulses are adjustable by the "stimulator rate" and "duration" mode controls 103.

In one stimulus/buffer protocol, a spiral track is produced on surface 24 of turntable 22 for a duration set by the programmed duration of the output signal of stimulator 68 (for example, 10 seconds), and stimulator 66 is programmed to produce a single output pulse of suitable duration (for example, 5 seconds) beginning some time after the start of the output signal of stimulator 68. The protocol is initiated, after turntable 22 has been activated and is rotating at a constant speed (for example, 33 rpm), by closing manual switch 98. This couples the output of power supply 96 to relay 84 common terminal 94. The next time that magnet 108 rotates into alignment with magnetic switch 76, switch 76 is momentarily closed, producing a brief short circuit across terminals 78, 80 of stimulator 68, thereby triggering stimulator 68 to generate its pre-programmed output signal. In this protocol, stimulator 68 is programmed by mode control 105 to produce a single 5 volt pulse, 10 seconds in duration, beginning immediately after the short circuit occurs across terminals 78, 80. Stimulator 68 ignores subsequent closings of switch 76 during the protocol, i.e., until stimulator 68 terminates its preprogrammed output pulse. Then, master switch 98 can be opened to disable the circuitry 42 before beginning another protocol.

The pulse produced by stimulator 68 activates relay 84, thereby coupling the output of power supply 96 to common terminal 102 of relay 82. Immediately after the output pulse of stimulator 68 begins, stimulator 66 is producing a zero volt output. Thus relay 82 couples the voltage applied by relay 84 to buffer valve 36, opening the valve to deliver the buffer solution to turntable surface 24.

A short time after magnet 108 activates switch 76, turntable 22 rotates magnet 110 into alignment with magnetic switch 74, momentarily closing it. The delay between the closings of switches 76, 74 is adjusted by varying the spacing between magnets 108, 110 and/or the speed of turntable 22. The mechanical arrangement to implement the delay may be simplified by activating magnetic switches 74, 76 with the same magnet (for example, magnet 108). The delay between stimulator output signals may also be controlled electronically via the delay control on stimulator 66. Stimulator 66 is programmed (by controls 103) to respond to the short-circuit produced across terminals 70, 72 by producing a single 5 volt output pulse having a duration of, for example, five seconds. Stimulator 66 ignores later closings of switch 74 which occur during its preprogrammed output pulse. The pulse produced by stimulator 66 activates relay 82, thereby switchably decoupling power from buffer valve 36 (and closing it) and coupling power to stimulating agent valve 32 to open the valve. Thus, valve 32 is open for the duration of the output signal of stimulator 66, thereby delivering the stimulating agent to rotating turntable surface 24 during that time.

At the end of the output pulse of stimulator 66, relay 82 is deactivated, thereby decoupling operating power from valve 32 and coupling the output voltage of power supply 96 to valve 36. Thus, stimulating agent valve 32 closes and buffer valve 36 re-opens to again deliver the buffer solution to rotating turntable surface 24 for the remainder of the protocol. The protocol terminates at the end of the output pulse of stimulator 68, which deactivates relay 84, thereby decoupling the output of power supply 96 from relay 82 (and valve 36) and closing buffer valve 36.

The spiral track generated in this protocol thus comprises an initial portion of buffer solution deposit, followed by a portion containing the single stimulating agent-generated deposit, and ending with another buffer solution deposit.

Figure 9:
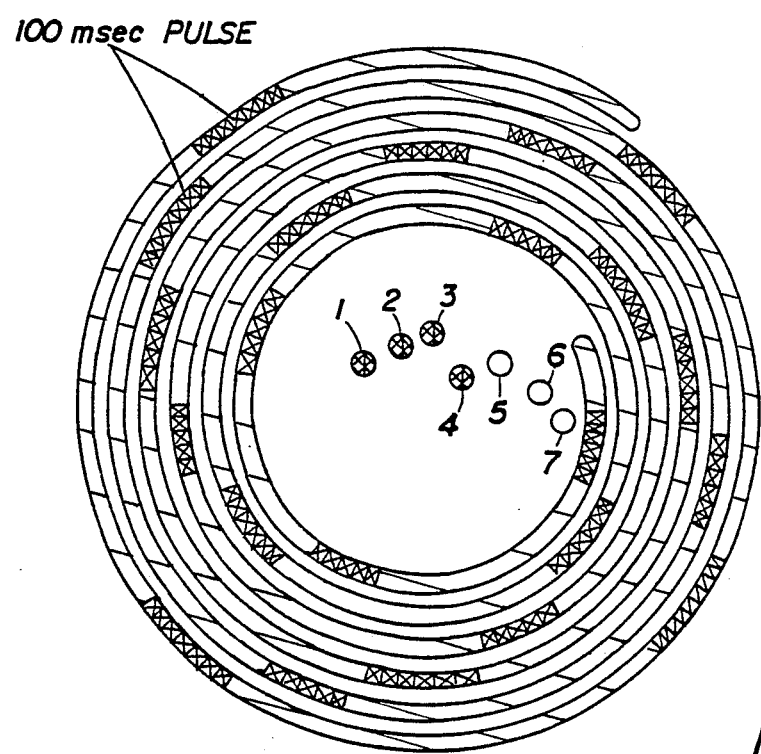
FIG. 9 is a diagrammatic representation of a spirogram.

In a second protocol, a series of alternating buffer and stimulating agent-generated deposits are made in a spiral track resembling that shown in FIG. 9. For this protocol, the Ext. single In ports 70, 72 of stimulator 66 are disconnected from magnetic switch 74, which is not used. Also, stimulator 66 is set to the "repetitive" operating mode, and the frequency and duration of the output pulses of stimulator 66 are programmed as desired (for example 2 Hz, 100 msec pulse width). In the repetitive mode, stimulator 66 is "free running", producing the programmed series of pulses nonsynchronized with the rotation of turntable 22.

Figure 8:
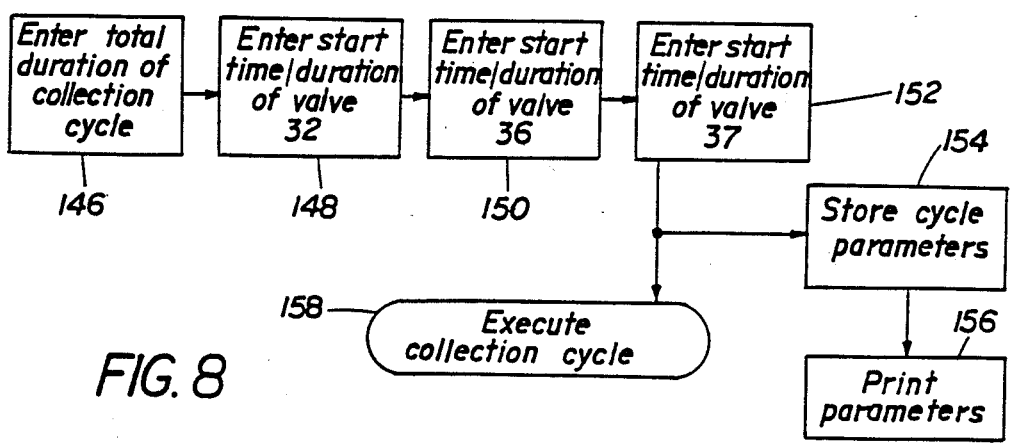
FIG. 8 is a computer protocol for use with the FIG. 7 circuitry.
Figure 6:
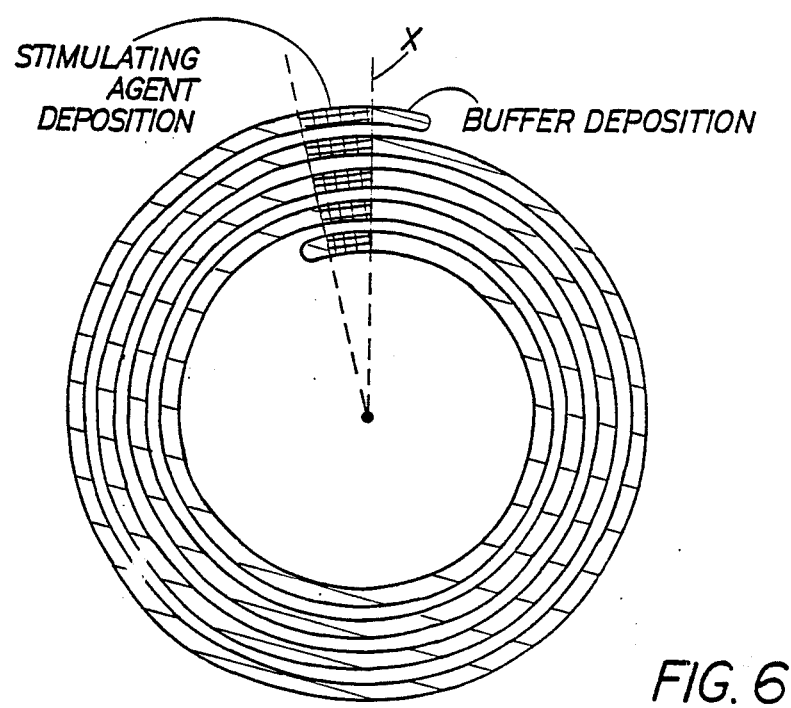
FIG. 6 is a diagrammatic representation of a spirogram.

This protocol is also initiated by closing switch 98, and stimulator 68 produces a single pulse (for example, 10 seconds in duration) when rotating magnet 108 momentarily closes switch 76. For the duration of the output pulse of stimulator 68, relay 82 is alternately activated and deactivated by the pulses produced by stimulator 66, thereby alternately opening relays 36, 32 to deposit a spiral track consisting of continuous series of alternating buffer solution deposits and stimulating agent deposits, as in FIG. 9. The relative durations of the deposits are adjusted simply by varying the frequency and pulse width of the output pulses of stimulator 66 with controls 103. This protocol terminates at the end of the output pulse of stimulator 68, which causes both valves 32, 36 to close by deactivating relay 84.

Referring also to FIGS. 5 and 6, valve control circuitry 42 is modified as shown in FIG. 5 to produce a buffer/stimulus protocol as shown in FIG. 6, in which one stimulating agent deposition is made during each revolution of turntable 22, with the series of stimulating agent depositions being aligned on the spiral track. In this protocol, magnetic switch 74 is again used. However, one terminal of switch 74 is connected to the (+) output of power supply 96, and the other to the "Synch Delay In" terminal 70*a* of stimulator 66. Terminal 70*a* is coupled through resistor R (for example, 270K ohms) to terminal 72*a*, which is connected to ground potential. The Ext. Single In terminals 70, 72 are unused. Stimulator 68 is connected and programmed as discussed above for the other protocols.

Stimulator 66 is programmed (by mode control 103, FIG. 4) to the "single" pulse mode. In this mode, stimulator 66 responds to each closure of magnetic switch 74 (by rotating magnet 110) by producing a pulse having a duration programmed by duration control 103. Thus, stimulator 66 activates relay 82 to open stimulating agent valve 32 once during each revolution of turntable 22, corresponding to each closure of switch 74. As shown in FIG. 6, the stimulating agent depositions begin on the same angular rotational position X of the turntable; that is, the stimulating agent depositions are aligned on the spiral track. This protocol also terminates at the end of the output pulse produced by stimulator 68.

Referring to FIG. 7, an alternate circuit 112 is shown which uses a computer 114 to control a number of valves (here, three valves 32, 36, 3, although a greater or fewer number of valves may be used). Computer 114 may be any suitable computer, for example, a personal computer (such as an Apple IIe® computer). A plurality of solid-state relays 116, 118, 119, corresponding to valves 32, 36, 37 are used in place of the mercury wetted contact relays 82, 84 of FIG. 4. Relays 116, 118, 119 (here, model 6321 solid state relays available from Crydom, Inc., of El Segundo, Calif.) are activated by control signals produced by the computer 114 at digital-to-analog (D/A) output port 120 via commercially available cables 122, 124. Relays 116, 118, 119 derive operating power from a 5 volt power supply 126.

Turntable 22 includes a single magnet 128 for momentarily closing magnetic switch 130 to provide computer 114 with a reference signal as to the rotation position of turntable 22. Magnetic switch 130, along with a manual switch 132, are electrically connected across analog-to digital (A/D) input port 136 of computer 150 via commercially available cables 138, 140, 142. Battery 134 (for example, 9 volts) and resistor 135 (1000 ohms) are connected in series with switches 130, 132 to apply an input signal to A/D port 136 when either switch closes.

The 12 volt DC power supply 144 is switchably connected to valves 32, 36, 37 via relays 116, 118, 119, respectively. The (+) output of power supply 144 is connected to the common terminal of each relay 116, 118, 119. The normally open terminal of relay 116 is connected to the (+) terminal of valve 32, the (+) terminal of valve 36 is connected to the normally open terminal of relay 118, and the (+) terminal of relay 119 is connected to valve 37. The (−) terminal of power supply 144 is connected to the (−) terminals of valves 32, 36, 37.

Referring to FIG. 8, in operation computer 144 is programmed to allow the operator to select the parameters of the superfusate collection cycles in a menu driven, step by-step fashion. In step 146, the operator enters the total duration of the collection cycle (that is, the time duration of the spiral track to be generated on turntable surface 24).

In step 148, the operator enters the parameters of operation for valve 32, for example, the number of times valve 32 is to be open during the cycle, the timing of each activation of valve 32 (with reference to the closure of switch 130 during turntable rotations), and the time duration of each activation of valve 32.

Likewise, in steps 150, 152 the operator enters the number, timing, and duration of each activation of valves 36, 37 during the collection cycle.

The parameters entered in steps 146, 148, 150, 152 may then be stored 154 (for example, on a floppy disk or on the hard disk of computer 114) for future reference. The parameters may also be graphed and printed 156.

The operator then initiates execution (158) of the collection cycle protocol programmed in steps 146, 148, 150, 152. The collection cycle is time referenced to the closing of switch 130 (by magnet 128 during the rotation of turntable 22) or by manually activating switch 132. Computer 114 senses, at A/D input port 136, the current produced in resistor 135 and responds by activating relays 116, 118, 119 at the times, in the sequence, and for the durations programmed in steps 146, 148, 150, 152. Each relay, when activated, switchably couples the 12 volt signal from power supply 144 to the associated valve 32, 36, 37, thereby activating (i.e., opening) the valve for the duration that the relay is activated by computer 114.

The device 20 is used to monitor the release of a substance by a substrate. The substrate can be, e.g., a biological structure surrounded by a cellular membrane; a protein; a polynucleotide; or a HPLC absorbant. The substance is immobilized by the substrate when exposed to one set of conditions, and released from the substrate when exposed to a second set of conditions. Where the substrate is a structure surrounded by a cellular membrane, the substance can be, e.g., ions ($Na^+$, $Ca^{+2}$) that the membrane retains in a cell or cell organelle until an electrical, chemical, or physical stimulus—the second set of conditions—causes channels to open up in the membrane, releasing the ions. Where the substrate is a protein, the substance can be, e.g., a second protein or a nucleotide that binds to the protein; some chemical or physical (e.g., temperature) change causes the substance to be released. A specific example is the release of the nucleotide GDP from a class of regulatory proteins termed "G proteins"; this release event occurs in response to the stimulation of a variety of cells by specific hormones and is a key process in the regulation of cellular functions. Where the substrate is a nucleotide, the substance can be, e.g., a protein that binds to the nucleotide under certain conditions (e.g., a gene repressor binding to a gene).

The substance can be labeled, e.g., radiolabeled, fluorescently labeled, so that the release of the substance can be monitored by determining the amount of label in the absorbance pattern. As an alternative, where the substance is a protein, an antibody-antigen interaction can be used to monitor the release of the substance.

A preferred use for the device is to monitor the release of ions through the membranes of subcellular, sub micron sized organelles such as photoreceptor cell disks, nerve terminal particles, T-tubule systems of skeletal muscle, and the endoplasmic reticulum of muscle, nerve, and endocrine cells. In general, the organelles are isolated and radioisotopically labeled with the relevant ions. The organelles are then supported on a depth filter matrix and allowed to equilibrate with a physiological buffer solution that flows into the sample chamber through the valve 32. The valve 32 is then closed simultaneously with the opening of valve 34, and the buffered solution in reservoir 38, generally containing a chemical agent (e.g., a drug; an endogenous cellular regulatory molecule such as cyclic nucleotides or inositol triphosphate; or other ions that change the electrical potential of the membrane) being tested or employed for its membrane channel opening properties, flows through the chamber and contacts the substance immobilized by the substrate. If the agent causes the release of the substance, the substance is carried away by the solution and exits the sample chamber through the solution outlet 27.

Simultaneous with (or preceding) the opening of the valve 34, the turntable 22 and the worm gear 30 are activated. The turntable rotates and the worm gear moves the sample chamber from the outside of the turntable towards the center. Solution flowing from the outlet 27 contacts a continuously moving restricted zone of the absorbant material 24, generating a fluid absorbance pattern in the form of spiral tracks (FIG. 1).

The time course and intensity of the ion channel opening can be measured by determining the quantity of radioactivity along the spiral tracks. The determination can be done by overlaying the dried absorbant material onto an X ray film and generating an autoradiographic image of the distribution of radioactivity along the spiral. The autoradiographic image is read by a densitometer or silver grain counting device and is then translated—using appropriate standards, information on track deposition speed, etc.—into a history of the release, i.e., the amount of the ion released at a given time subsequent to the initiation of the stimulus.

The time resolution achieved is dependent on a number of factors, including the flow rate of the solution and the rotation rate of the turntable; the faster the rotation rate or the faster the flow rate, the better the time resolution. In general, solution flow rates exceeding 0.1 ml/sec are desirable in order for the substance released by the substrate to rapidly exit the sample chamber. As the solution flow rate is increased, e.g., to greater than 1 ml/sec, the time resolution of the device is further improved, but a thicker, more absorbant substance absorbant is required, since if too much solution contacts the absorbant material, the tracks will spread out and, in some circumstances, run together. The time resolution desired will depend upon the particular substrate-substance combination being analyzed; resolution as low as 2 msec is achievable with the device.

To obtain an 8 msec time resolution using the device 20 (with the absorbant material being 1 mm thick chromatography paper), the nitrogen pressure is adjusted so that the flow rate is 0.25 ml/sec; the turntable speed is set by programming the DC stepping motor so that the surface of the absorbant material constantly moves at 400 mm/sec with respect to the solvent stream; and the inward radial movement of the sample chamber is fixed at 0.5 cm/sec. A 5 mm track is deposited, with the individual tracks being separated by approximately 5 mm. Each approximately 0.4 cm corresponds to 8 msec. Thirty seconds worth of solution and concomitant biological information are readily captured under these conditions.

To obtain a 16 msec time resolution but a longer spiral track recording time, either the flow rate and/or the turntable speed can be reduced. The relationship between time resolution and the latter two parameters is not necessarily linear; one skilled in the art would readily know how to adjust the parameters to achieve the target resolution. Similarly, a 4 msec time resolution can be achieved by either increasing the flow rate and/or increasing the turntable speed.

Another variable that can be adjusted using the device 20 is the exposure time of the immobilized substance to the agent. The valve 36 can be opened for varying lengths of time, e.g., 2 msec, 5 msec, 10 msec, and then closed, with the simultaneous reopening of the valve 32 so that the non agent containing buffered solution again flows through the sample chamber. In this way, the opening and subsequent closing of the channels in the cellular membranes, and/or the release of neurotransmitters, etc., can be continuously monitored. Moreover, alternating aliquots of agent containing solution from reservoir 38 and non agent containing buffer solution from reservoir 34 can be flushed through the sample chamber, and the response of the cellular membranes likewise monitored.

Following is an example demonstrating how a standard spiral track can be generated; no substrate-substance combination was used.

Example 1: Generation of Standard Spiral Track

An 11 inch diameter disc (1 mm Whatman chromatograph paper) is placed on the turntable, and the sample chamber is positioned so that the effluent is aligned precisely with the radius that defines the spiral.

In the center of the filter paper is added 10λ of standards containing the following $^{45}Ca^{+2}$ concentrations in cpm/ml: (1) $8.8 \times 10^6$; (2) $4.4 \times 10^6$; (3) $1.75 \times 10^6$; (4) $8.8 \times 10^5$; (5) $3.5 \times 10^5$; (6) $1.75 \times 10^5$; and (7) $7.0 \times 10^4$.

In one reservoir is placed 10 ml of $^{45}Ca^{+2}$, $1.8 \times 10^6$ cpm/ml, in standard MOPS/KCl buffer. In the second reservoir is placed 30 ml of $^{45}Ca^{+2}$, $1.8 \times 10^5$ cpm/ml, in the same buffer. No substrate-substance combination is placed in the sample chamber.

The relay-driven electrical system is adjusted to generate 100 msec pulses of the high cpm $^{45}Ca^{+2}$ solution (first reservoir) interspersed with 400 msec sprays of the low cpm $^{45}Ca^{+2}$ solution (second reservoir). Two pulses are thus generated per second. The flow rate is adjusted to approximately 0.25 ml/sec (10 psi of pressure are used), and the turntable speed is set at 33⅓ rpm (no stepping motor is used). Approximately 10 sec worth of data are recorded, in the form of a spiral track.

Immediately after generating the spiral track, the filter paper is frozen between two prechilled ($-70°$ C.) glass plates; lyophilized for 90 minutes; and air dried for an additional 5 minutes at room temperature. The filter paper is then overlayed with x-ray film (Fuji RX, 14×17 inches), and the film is allowed to develop for 48 hours at $-70°$ C.

FIG. 9 is the autoradiogram that is generated. The seven standard spots have developed, with the standards having the lowest cpm of $^{45}Ca^{+2}$ displaying the lowest intensity and the standard having the highest cpm of $^{45}Ca^{+2}$ displaying the greatest intensity. The spiral track with well-defined 10 msec pulses is clearly visible. The intensity of the spiral track region within each 100 msec pulse corresponds to the intensity within standard 3; the intensity of the remaining portions of the track correspond to the intensity within standard 6. Both the 100 msec pulse portions and the remaining portions show good consistency. Because, in this instance, the turntable is operating at a constant angular velocity (RPM) rather than a constant linear velocity of track deposition, the length of the 100 msec pulse, as shown on the antoradiagram, decreases as the track spirals inward because the linear velocity of track deposition decreases; and the width of the track increases because more fluid is absorbed per unit of track length.

Figure 10:
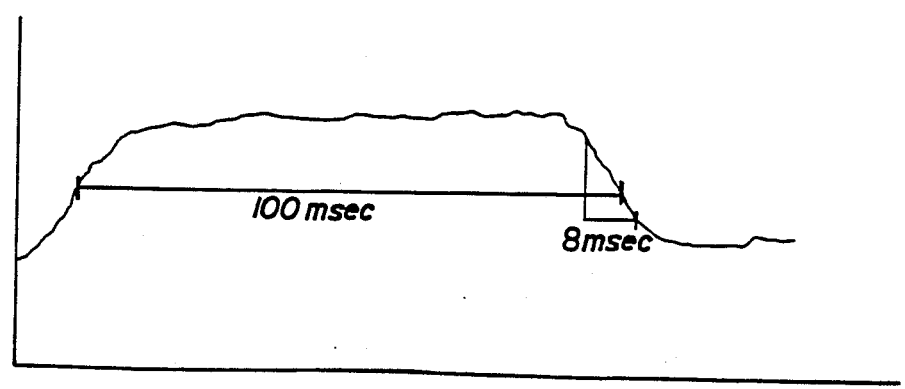
FIG. 10 is a diagrammatic illustration of the time resolution of a 100 msec. $^{45}Ca^{+2}$ pulse.

Referring to FIG. 10, a typical 100 msec pulse is scanned with a densitometer (550 nm). Each 14 cm on the X axis corresponds to 100 msec. The time resolution achieved is approximately 8 msec. The time resolution is defined as the time constant for transition from the low concentrations of $^{45}Ca^{+2}$ to the new, higher steady state value of the concentration of $^{45}Ca^{+2}$ achieved during the 100 msec pulse. The time constant $\uparrow$ is defined as employed by the equation $$\Delta Abs_t = \Delta Abs_{total}[1 - e^{-(t\uparrow)}]$$

where t is the time in msec from the start of the pulse $\Delta Abs_t =$ the net spectrophotometric absorbance change at time t, and $\Delta Abs_{total}$ is the total absorbance change achieved at steady state. In actuality, $\uparrow$ thus defines the time required for about ⅔ of the absorbance change to occur.

The device has been used to generate repetitive release of $^{45}Ca^{+2}$ from photoreceptor discs in response to repetitive delivery and removal of cGMP. The experimental details are generally the same as those described in this Example and Example 3 (loading the discs).

Other Embodiments

Other embodiments are within the following claims. For example, the absorbant material can also be arranged to continuously move in a linear direction (e.g., between two rollers), or can be mounted on a rotating drum. The advantage of these alternatives is that the rate at which the surface of the material is moved does not need to be continuously altered to generate an absorbance pattern in which a given length corresponds to a constant time frame.

As an alternative to using the more preferred absorbant material arrangement of device 20, a quick-moving fraction collector of the type described by Forbush, (1984) Anal. Biochem., 140, 495, can also be used with the sample chamber 26. The following examples use such an arrangement.

Example 2: Release of Na+ from Bovine Rod Outer Segment Discs Stimulated with 8-Br-cGMP Purified bovine rod outer segment disks were prepared in dim red light from frozen retinas (Hormel) using the procedure described by Puckett et al., (1985) Biochem. 24, 390–400. Briefly, osmotically intact crude disks were obtained from bovine retinal rod outer segments by hypoosmotic shock, floated on a 5% Ficoll 400 solution, and separated into two distinct components, the "R Band" and "W-band", on a linear Ficoll density gradient. The major component was the R-band, and comprises the isolated disks. Disks (8 to 15 mg protein/ml) were stored in the dark at 4° C. in a phosphate buffer (buffer A; 0.1 M $KH_2PO_4$, 60mM NaOH, and 5mM 2-mercaptoethanol, pH 7.0) for up to four weeks without loss of activity.

By the means described below, chemical excitation of vesicle-associated, cGMP-activated channels is experimentally controlled in analogy with the way an electrophysiologist controls electrical excitation of voltage-gated ion channels.

Buffer A and buffer B (buffer A plus 25 mM 8-Br cGMP) are held in reservoirs 34 and 38, respectively. The two solutions are separately delivered under nitrogen pressure (60-110 psi) to the inlets of the valves 32 and 36.

Solution exiting the sample chamber through outlet 27 is continuously collected in closely juxtaposed glass vials (½ dram shell vials, Rochester Scientific, Rochester, N.Y.) mounted on the perimeter of a phonograph turntable (the entire circumference of an 11" diameter platter holds 63 vials). Collection intervals of 56 msec/fraction correspond to a turntable speed of 16 rpm; 33 rpm generates 26 msec/fraction; and 78 rpm generator 11.3 msec fractions. Collection intervals of 0.5 sec employed an external variable speed motor geared to the turntable.

The collection of superfusate is synchronized with the solution delivery to the vesicles by initiating the "stimulus protocol" via magnetic reed switches that sense the position of permanent magnets fixed to the rotating turntable, as previously discussed. The configuration allows flexibility with regard to the stimulation protocol.

A few ug of purified disk membrane vesicles, preloaded with $^{22}Na^+$, are retained within the housing in the center of a 6 mm diameter glass fiber filter (depth filter 50) sandwiched between filters 48, 52, as follows.

Sections (2.5 cm) of 200 ul glass micropipettes (#4624, Clay Adams, Parsippany, NJ) were heat-sealed at one end and 200 uCi (20 ul) of $^{22}NA^+$ (1000 ci/g, New England Nuclear, Cambridge, MA) were added with a 50 ul Hamilton syringe to the bottom of this tube and dried overnight at 90° C. The tube was placed on ice; purified disks (80 ug protein in 5-10 ul of phosphate buffer) were added to the bottom of the tube using a 5 ul Hamilton syringe. The tube was shaken gently on a rotating table for 4 to 24 hrs at 4° C. to allow equilibration of $^{22}Na^+$. The disks were handled in dim red light (Kodak no. 1 safelight filter, 15 W).

All procedures were performed in the light at ambient temperature (24° C.) except where noted. Nitrocellulose filters (S.C., 25 mm diameter, Millipore Corp, Bedford, MA) were prerinsed as follows to remove incorporated detergent. Biobeads (Bio-Rad Corp.) were washed with methanol. Eight S.C. filters were placed in a slurry of 1.8 g of Biobeads in 6 mls of distilled water in a sealed 60×15 mm plastic petri dish, and subjected to gentle agitation on a laboratory rotator overnight at room temperature. Small (6 mm diameter) circles were then cut from the filters with a stainless steel punch; the circles were dried and could be stored indefinitely. Whatman 25 mm GF/F filters were not prerinsed before 6 mm circles were cut.

The filter sandwich (Millipore S.C., Whatman GF/F, Millipore S.C.) was prerinsed with 1 ml ice-cold phosphate buffer, and held between the two stainless steel washers. An aliquot of disks loaded with $^{22}Na^+$ (8 ug protein in 0.5 to 1.0 ul) is retained within the center 3 mm region of the filter sandwich. Disk vesicles trapped on the filters were washed with 1 ml of ice-cold buffer A delivered from a syringe to remove most of the extravesicular $^{22}Na^+$. The filter sandwich containing trapped disks was then transferred to the sample chamber and placed on a stainless steel washer 46 within the chamber with the disks facing the mixing chamber 45 between the two valves 32, 36. A stainless steel mesh screen (400 mesh) is placed within the chamber followed by an additional stainless steel washer 56, and the threaded efflux outlet fitting is used to secure the filters in place. Once secured within the chamber, the disks are superfused for 5 secs with buffer (25 ml) to more completely remove excess radiolabel and for a determination of superfusate flow rate (4-6 ml/Sec was the acceptable range). Valve 32 is then shut, and valve 36 opened, and the disks are superfused with buffer B.

The protocol was followed three times, once collecting 26 msec fractions, the second time 53 msec fractions, and the third time 0.5 sec fractions. Manual collections of superfusate (0.5 sec fractions) were timed with an electronic metronome. These fractions were collected directly in the shell vials. Fractions collected at 53 msec intervals were collected directly into the shell vials on the rotating turntable, and transferred to another set of vials for gamma radiation counting. Following constant superfusion with 8-Br-cGMP containing buffer B, the filter sandwich with trapped disk vesicles was removed immediately and counted to determine the $^{22}Na^+$ that remained associated with the disks. The amount of $^{22}Na^+$ released into the superfusate and collected in each fraction was expressed as a percentage of the total $^{22}Na^+$ initially associated with the disks.

Figure 11:
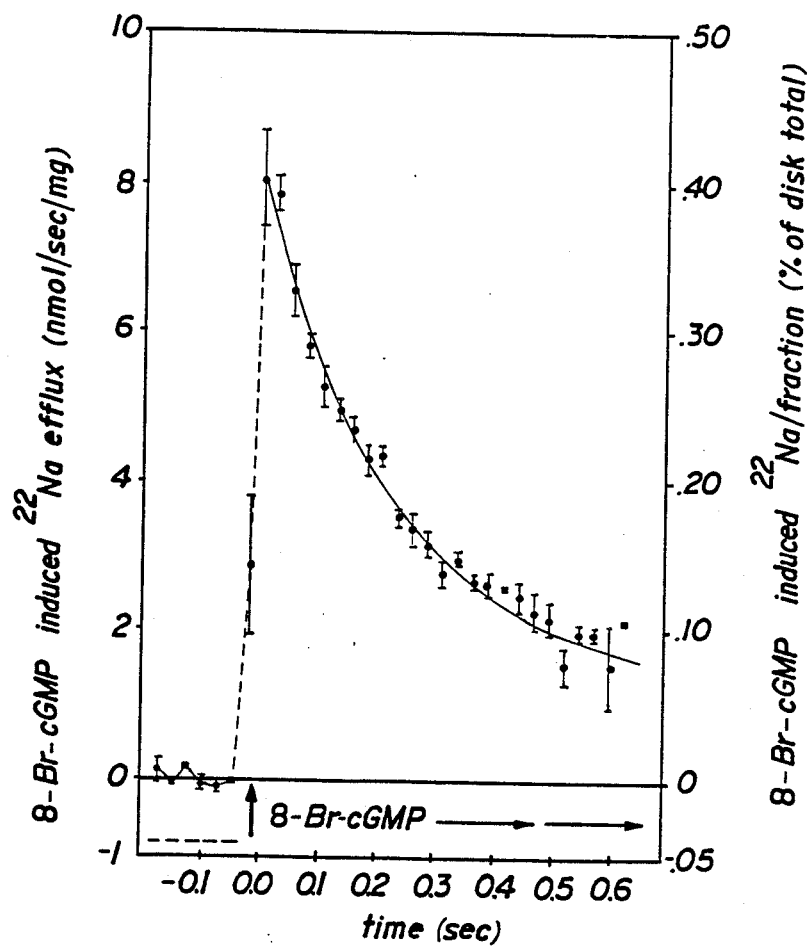
FIGS. 11-13 are diagrammatic representations of the 8-Br-cGMP generated release of $^{22}Na^+$ from bovine rod outer segment disks.
Figure 13:
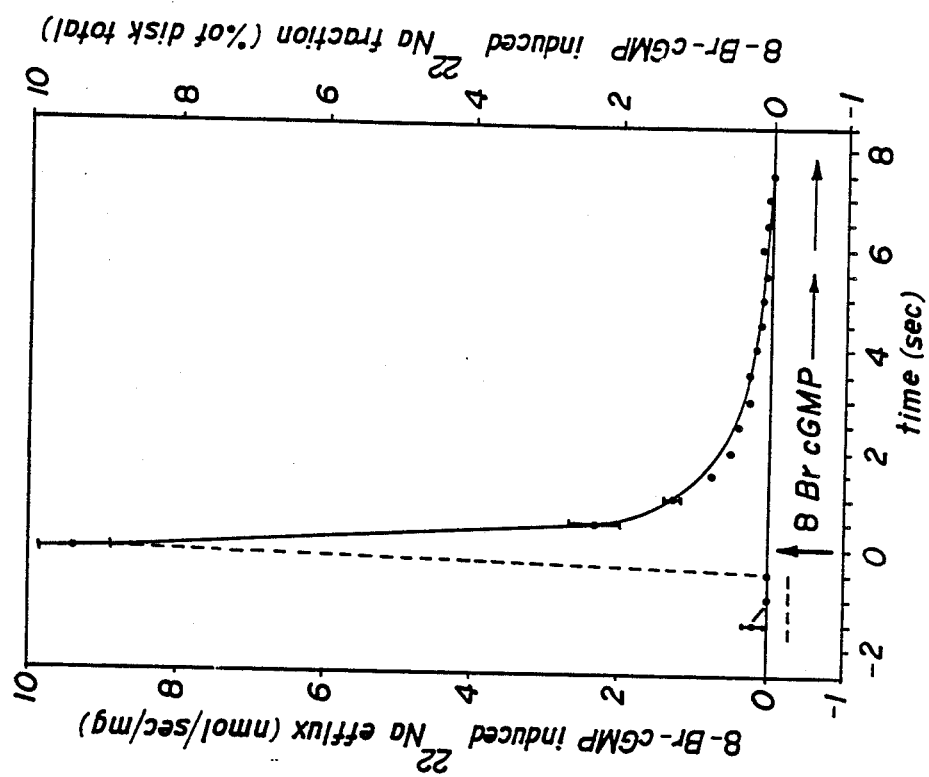
Figure 12:
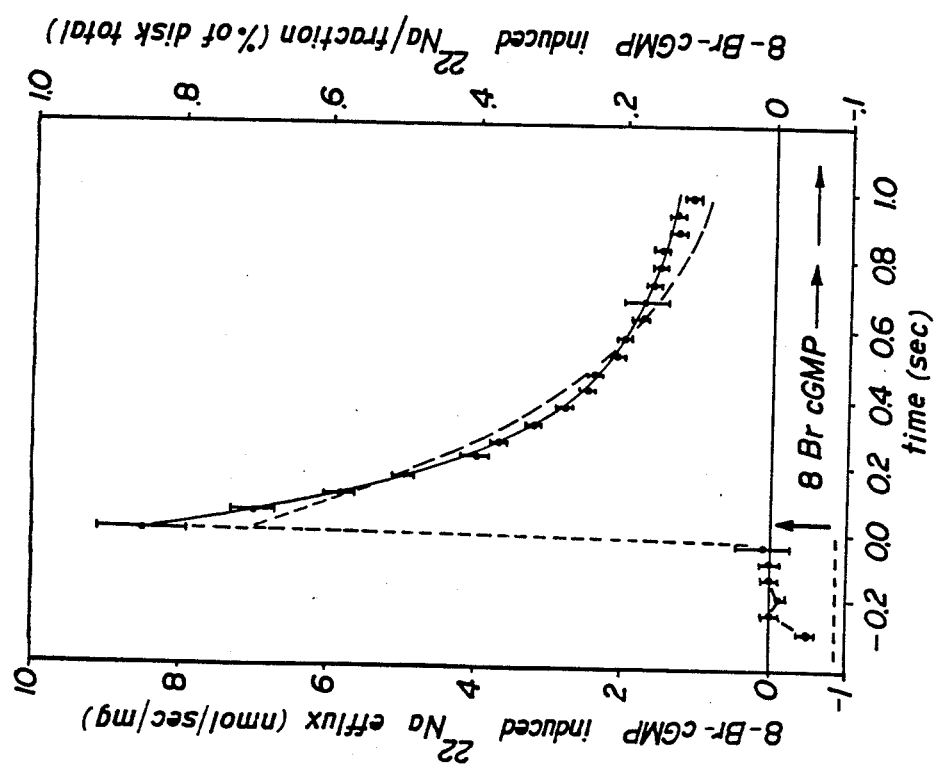
Figure 15:
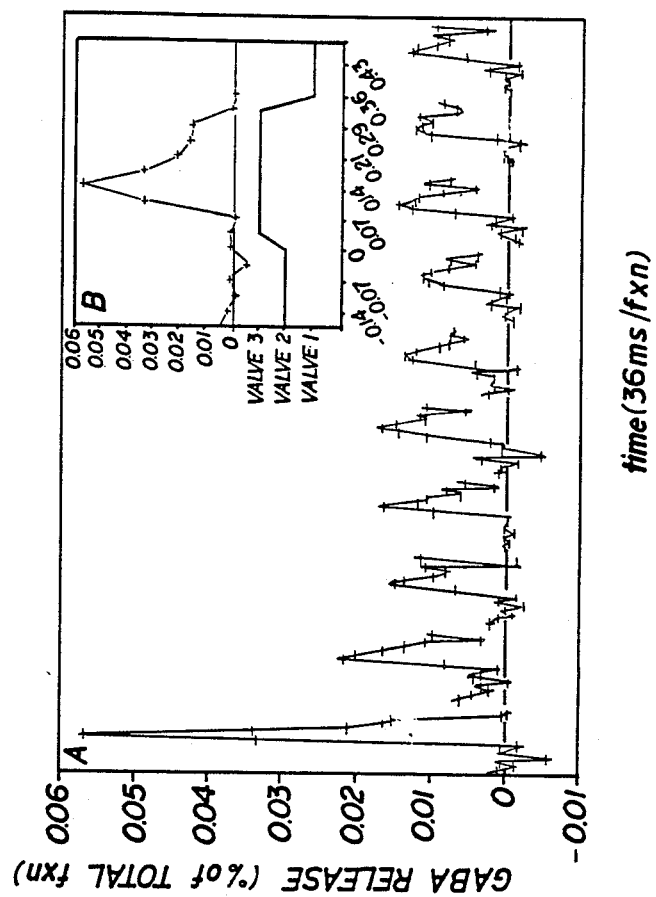
FIG. 15 is a diagrammatic representation of potassium-generated release of GABA from brain nerve terminal preparations.

Referring to FIGS. 11 through 13, the vertical arrows denote the point of the switch to continuous superfusion with 25 uM 8-Br-cGMP. The effluent containing released $^{22}Na^+$ was collected as discrete fractions. FIG. 11 displays fractions continuously collected at 26 msec intervals; FIG. 12, 53 msec intervals; and FIG. 13, 0.5 sec intervals. The solid curves denote the best fit of the decay of 8-Br-cGMP-stimulated $^{22}Na^+$ release to biphasic exponential kinetics. The dashed curve (----) of FIG. 12 is the best fit of the data to a single exponential decay. The scalar value of $^{22}Na^+$ efflux, denoted by the dashed horizontal lines represents the "basal" level of $^{22}Na^+$ efflux prior to stimulation with 8-Br-cGMP. Each time point was an average of multiple experiments.

Example 3: Release of $Ca^{+2}$ from Bovine Rod Outer Segment Disks Stimulated with 8-Br-cGMP The protocols for $^{45}Ca^{2+}$ efflux measurement were similar to that for the $^{22}Na^+$ efflux studies, with the following differences. A lower specific activity of commercially available $^{45}Ca^{2+}$ (New England Nuclear #NEZ-013, -25-35 Ci/g) limited the superfusate fraction collection interval to ~90 msec, to obtain enough dpm per fraction to permit reliable measurements. Because phosphate ion binds to and precipitates $Ca^{2+}$, the disk vesicles were washed and resuspended in a phosphate-free buffer (buffer C; 0.15 M KCl, 15 mM MOPS, 5 mM 2-mercaptoethanol, titrated to pH 7.0 with KOH), by the following procedure performed under dim red light at 0-4° C. Purified disk vesicles, 4-6 mg (stored in buffer A as described above) were diluted into 35 ml of buffer C. The suspension was subjected to centrifugation at 17,500 rpm for 30 min. The pellet was resuspended in 35 ml of buffer C, and the centrifugation was repeated. The final pellet was resuspended to a [protein] of ~10 mg/ml in buffer C and incubated overnight in the dark at 4° C., at a [protein] of 1.25 mg/ml; and a final volume of 40 ul. This suspension was incubated for 30 minutes at 37° C.; 8 uL of the suspension was withdrawn and diluted into 40 uL of buffer C. The diluted suspension was then loaded onto the filter stack as in the $^{22}Na^+$ protocol described above; the filter stack in the loading chamber was rinsed with three 300 ul aliquots of buffer C to remove most of the extravesicular $^{45}Ca^{2+}$.

Subsequent steps were the same as detailed above in the $^{22}Na^+$ efflux measurement protocol, but buffer C was substituted for buffer A in reservoir 34, reservoir 36 contained buffer C+25 um 8-Br-c6MP, the nitrogen pressure was 40 psi, and the flow rate was 2-3 ml/sec. Fractions were collected every 94 msec, were transferred to scintillation vials, 31 10 volumes of Hydrofluor (National Diagnostics, Manville, NJ) were added, and the samples were counted in a beta scintillation counter. Total levels of $^{45}Ca^{2+}$ incorporated into the disk vesicles were determined by subjecting the filter stack to beta counting after the superfusion was completed.

To determine the effect of $Na^+$ on cyclic nucleotide-stimulated $^{45}Ca^{2+}$ efflux, varying concentrations of NaCl (10 mM, 20 mM, and 40 mM) were substituted for equimolar amounts of KCl in buffer C. This modified buffer was then substituted for buffer C in washing the disks free of phosphate, actively loading the disks with $^{45}Ca^{2+}$, and performing the superfusion.

Figure 14:
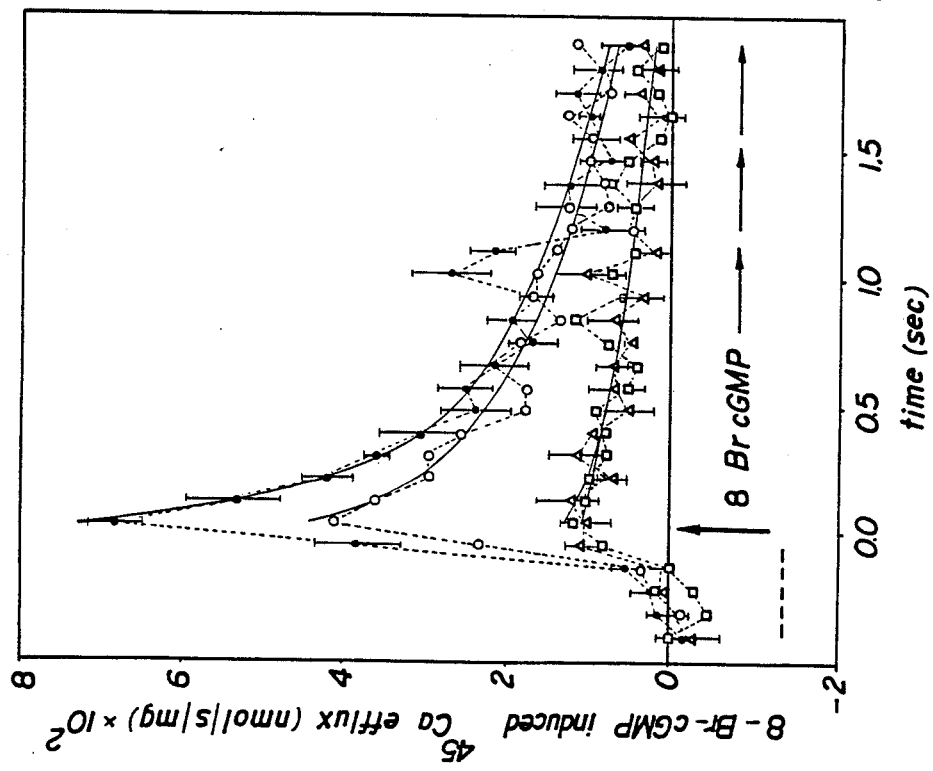
FIG. 14 is a diagrammatic representation of the 8-Br-cGMP generated release of $^{45}Ca^{+2}$ from bovine rod outer segment disks.

Referring to FIG. 14, the efflux of $^{45}Ca^{+2}$ caused by different concentrations of NaCl substituted for equimolar amounts of KCl in buffer C ($Na^+$ free, •; 10 mM $Na^+$, o; 20 mM $Na^+$, Δ; 40 mM $Na^+$, □) is plotted against time. The solid curves denote the best fit of the decay of the response to biphasic exponential decay kinetics. Each data symbol is the mean of 3 separate experiments. For visual clarity, error bars are displayed only for the experiments performed in 0 mM and 40 mM $Na^+$, but were typical of the other sets of experiments. The scalar value of $^{45}Ca^{+2}$ efflux denoted by the dashed horizontal lines (lower left) represents the basal level of $^{45}Ca^{+2}$ efflux prior to stimulation with 8-Br-cGMP.

In $Na^+$ free solution, 8-Br-cGMP stimulates the release of $^{45}Ca^{+2}$ in an analogous manner to $Na^+$ release (discussed above). Extravesicular $Na^+$ inhibits 8-Br-cGMP stimulated release of $^{45}Ca+2$, with a relatively steep concentration dependence.

Example 4: Use of the Rapid Superfusion Method to Measure Kinetics of GABA Secretion from Rat Brain Nerve Endings Rat brain nerve endings, known as synaptosomes, are prepared fresh for each experiment by conventional methods. The final synaptosomal pellet is resuspended in a physiological salt solution with an EGTA-Ca buffer (designated 5K) that maintains the external free Ca concentration at sub-micromolar levels. The suspension of these vesicles contains between 5 and 7 mg of protein per ml. One ml of the suspension is diluted into 9 ml of 5K, and shaken continuously to provide the oxygen necessary for respiration. After a 5 minute equilibration period, the synaptosomes are loaded with the radiolabeled transmitter as follows. 100 ul of the synaptosome suspension are combined with 5-uCi of $^3$H-GABA for a period of ten minutes; this interval optimizes both total GABA uptake and the fraction of $^3$H-GABA available for release.

The radiolabeled synaptosomes are applied to a glass fiber filter and accompanying filter assembly by pushing the suspension through a teflon fitting (5 mm i.d.) that houses a filter assembly composed of the following:
 a. a stainless steel washer;
 b. a millipore SC membrane circle;
 c. a GF/B glass fiber filter circle;
 d. a second millipore SC membrane circle;
 e. a stainless steel screen for support; and
 f. a second stainless steel washer.

The synaptosomes are loaded on the filter as described in Examples 2 and 3. The effluent contains 5K plus any $^3$H-GABA not taken-up by the synaptosomes.

The loaded filter wafer is transferred to sample chamber that has been modified in two ways from the one used in Examples 2 and 3. The first modification is the addition of a GF/B glass fiber "prefilter" in the superfusion chamber that is placed between the first (top) S.S. washer and the loaded filter wafer. The GF/B decreases the fluid stream artifact due to radiolabel released into the effluent associated with the valve switching event. The other modification is the addition of a millipore RA membrane "postfilter" between the bottom of the loaded filter wafer and the stainless steel support screen. The postfilter has a small pore size and acts as a "safety net," catching any micron-size particles that may be dislodged from the filter wafer during the superfusion. These modifications add about 10 ul to the volume of the superfusion chamber and result in a increase in wash-out time, but assist in keeping the valve switching artifact acceptably small. The entire assembly is held in place in the superfusion chamber with a teflon exit fitting (58-62) wrapped with two layers of teflon pipe-thread tape.

Superfusion is controlled with the Apple IIe microcomputer routine, using a three valve version of the original General Valve two-valve mixing chamber assembly; control circuitry was modified to accomodate the additional valve. The superfusion is conducted with a nitrogen pressure of 37 psig, resulting in highly reproducible flow rate of 1.3-1.5 ml/sec, giving synaptosome-loaded chamber wash-out times of 40-50 ms. Any $^3$H-GABA remaining on the filters is washed away by prior superfusion for two five second periods with 5K. The release event is recorded by collecting the effluent in the rotating fraction collector; a turntable speed of 33 rpm 1800 ms/rev) gives 50 fractions of 36 ms each. Release of GABA is evoked by switching from a basal superfusion buffer (designated 5K/Ca to a $K^+$-rich superfusion buffer (designated 110K/Ca). The elevated $K^+$ concentration in 110K/Ca causes depolarization of the synaptosomal membrane, activating a number of transport processes that allow $Ca^{++}$ to enter the vesicles, ultimately resulting in Ca-dependent release of GABA. The synaptosomes are stimulated in this fashion for a brief period sufficient to maximally evoke the release event, and the membrane is subsequently repolarized by switching to a basal superfusion buffer.

The rapid superfusion apparatus can be programmed to deliver a variable frequency train of depolarizing pulses to the synaptosomes. In this case, the final superfusion buffer must be 5K, that is, it must be a basal buffer with the EGTA Ca-buffer that maintains the external free Ca concentration in the sub micromolar range. Without this buffer, the release process rapidly inactivates, probably due to the accumulation of Ca within the synaptosomes that in turn results in inhibition of the release process. Including this low Ca buffer in the external solution during prolonged periods of rest relieve the accumulation of Ca inside the synaptosomes. The results of such a train of pulses (FIG. 13) show that after a relatively large initial pulse, the Ca-dependant component of GABA release becomes relatively constant for at least 9 pulses. As shown in the inset, each pulse lasts 900 ms: a 350 ms period of superfusion by 5K/Ca (valve 2), followed by 350 ms of superfusion by 110K/Ca (valve 3), and a final 200 ms superfusion by 5K (valve 1). The flow of buffer is then turned off, and the apparatus is poised to collect a second pulse of 900 ms in duration after an appropriate wait (typically ~20 sec). The program takes account of the position of the 25 vials on the fraction collector that were filled during the first pulse, and will not begin superfusion until fraction 26 is cued under the effluent fitting, so that no overlap of pulses occurs.

I claim:

1. A device for monitoring the release of a substance from a substrate, said device comprising
   a sample chamber adapted to be connected to a solution source and through which a solution supplied by said solution source can flow, said sample chamber comprising a retainer for holding a substance immobilized by a substrate while said supplied solution flows in contact with said immobilized substance and removes any said substance released from said substrate;
   a solution collector positioned to receive the solution flowing from said sample chamber and including a substance absorbant having an exposed face and means for supporting said substance absorbant,
   said sample chamber including means for directing a stream of said solution from said sample chamber into contact with a portion only of said exposed face of said substance absorbant; and
   means for continuously moving the location of said contact of said stream with respect to said exposed face of said substance absorbant.

2. The device of claim 1, said sample chamber comprising flow paths for said solution to flow from said solution source to said solution collector, a first said flow path passing through said retainer, a second relatively unobstructed flow path not passing through said retainer but merging with said first flow path after said first flow path passes through said retainer.

3. The device of claim 1 wherein said means for continuously moving comprises a rotating disc holding said substance absorbant.

4. The device of claim 1 wherein said substrate comprises a structure surrounded by a biological membrane and wherein said substance is released through said biological membrane.

5. The device of claim 1 wherein said retainer comprises a depth filter.

6. The device of claim 5 wherein said depth filter comprises a glass fiber filter.

7. The device for monitoring the release of a substance from a substrate, said device comprising
   a sample chamber adapted to be connected to a solution source and through which a solution supplied by said solution source can flow,
   said sample chamber comprising a retainer for holding a substance immobilized by a substrate while said supplied solution flows over said immobilized substance removing any said substance released by said substrate, and flow paths for said solution to flow from said solution source to a solution collector, a first said flow path passing through said retainer, a second relatively unobstructed flow path not passing through said retainer but merging with said first flow path after said first flow path passes through said retainer; and
   said solution collector positioned to receive the solution from the merged flow paths.

8. The device of claim 7 wherein said substrate comprises a structure surrounded by a biological membrane and wherein said substance is released through said biological membrane.

9. A device for monitoring the release of a substance from a substrate, said device comprising
   a solution source;
   a sample chamber adapted to be connected to said solution source and through which a solution supplied by said solution source can flow, said sample chamber comprising
   a retainer for holding a substance immobilized by a substrate while said supplied solution flows in contact with said immobilized substance and removes any said substance released from said substrate, and
   a plurality of valves corresponding to a plurality of solutions, said valves being responsive to control signals to deliver the solutions corresponding thereto to said sample chamber,
   said solution source including means for applying the control signals to said valves, said control signal applying means being programmable to selectively control the timing and duration of the delivery of solution by each valve; and
   a solution collector positioned to receive the solution that has flowed over said retainer in said sample chamber.

10. The device of claim 9 wherein said control signal applying means comprises
    (a) means for generating a valve activating signal,
    (b) means for generating a valve enable signal to enable said valve activating signal to be coupled to said plurality of valves, and
    (c) means for switchably coupling said enabled valve activating signal to said plurality of valves to selectively cause said valves to deliver their respective solutions to said sample chamber, said coupling means being programmable to vary the timing and duration of the activation of each said valve.

11. The device of claim 10, said solution collector being positioned to receive the solution flowing from said sample chamber and including a substance absorbant having an exposed face and means for supporting said substance absorbant, said sample chamber including means for directing a stream of said solution from said sample chamber into contact with a portion only of said substance absorbant; and said device further comprising means for continuously moving the location of said contact of said stream with respect to said exposed face of said substance absorbant.

12. The device of claim 11 wherein said means for continuously moving comprises a rotating disc holding said substance absorbant, and wherein said valve enable signal generating means is synchronized with the rotation of said rotating disc.

13. The device of claim 12 wherein said means for switchably coupling said enabled valve activating signal to said plurality of valves is also synchronized with said rotation of said rotating disc.

14. The device of claim 11 wherein (a) said means for continuously moving comprises a rotating disc holding said substance absorbant
(b) the delivery of said stream of solution forms a pattern on said substance absorbant;
(c) said valve enable signal generating means is synchronized with the rotation of said rotating disc to produce said valve enable signal for a duration equal to the time required to generate said spiral pattern; and
(d) said means for switchably coupling the valve activating signal to said plurality of valves comprises: means for producing an output signal having a first state corresponding to the activation of a first one of said plurality of valves and a second state corresponding to the activation of a second one of said plurality of valves, the relative timing and durations of the first and second states being programmable; and, means for coupling said valve activating signal to said first valve in response to said first state of said output signal and coupling said valve activating signal to said second valve in response to said second state of said output signal.

15. The device of claim 14 wherein said output signal producing means is programmed to produce a series of pulses of said second state thereof during the formation of said pattern.

16. The device of claim 14 wherein said output signal producing means is also synchronized with the rotation of said rotating disc and is programmable to produce a pulse of the second state thereof at a predetermined time within the duration of said valve enable signal.

17. The device of claim 16 wherein said output signal producing means is programmed to produce a pulse of said second state thereof during each revolution of said rotating disc, each said pulse being synchronized with the rotation of said rotating disc.

18. The device of claim 16 wherein the pulses produced during each revolution of said rotation disc are synchronized to be aligned on said pattern.

* * * * *